United States Patent
Webb et al.

[11] Patent Number: 6,166,385
[45] Date of Patent: Dec. 26, 2000

[54] MULTI-PHOTON LASER MICROSCOPY

[75] Inventors: Watt W. Webb, Ithaca, N.Y.; Chris Xu, Summit, N.J.

[73] Assignee: Cornell Research Foundation, Inc., Ithaca, N.Y.

[21] Appl. No.: 09/029,589

[22] PCT Filed: Sep. 18, 1996

[86] PCT No.: PCT/US96/14519

§ 371 Date: Jun. 11, 1998

§ 102(e) Date: Jun. 11, 1998

[87] PCT Pub. No.: WO97/11355

PCT Pub. Date: Mar. 27, 1997

Related U.S. Application Data

[60] Provisional application No. 60/003,957, Sep. 19, 1995.

[51] Int. Cl.$^7$ ................................................. G01N 21/39
[52] U.S. Cl. ................................ 250/458.1; 250/459.1; 250/461.1
[58] Field of Search ........................... 250/458.1, 459.1, 250/461.1

[56] References Cited

U.S. PATENT DOCUMENTS

| | | |
|---|---|---|
| 4,170,736 | 10/1979 | Wessel . |
| 4,405,237 | 9/1983 | Manuccia et al. . |
| 4,407,008 | 9/1983 | Schmidt et al. . |
| 4,464,761 | 8/1984 | Alfano et al. . |
| 4,466,080 | 8/1984 | Swainson et al. . |
| 4,471,470 | 9/1984 | Swainson et al. . |
| 4,631,581 | 12/1986 | Carlsson . |
| 4,734,578 | 3/1988 | Horikawa . |
| 4,786,170 | 11/1988 | Groebler . |
| 4,791,310 | 12/1988 | Honig et al. . |
| 4,792,341 | 12/1988 | Kozikowski et al. . |
| 4,827,125 | 5/1989 | Goldstein . |
| 4,838,679 | 6/1989 | Bille . |
| 4,863,226 | 9/1989 | Houpt et al. . |

(List continued on next page.)

FOREIGN PATENT DOCUMENTS

| | | |
|---|---|---|
| 152072 | 8/1985 | European Pat. Off. . |
| 0 666 473 A1 | 8/1995 | European Pat. Off. . |
| 35 05 728 | 9/1985 | Germany . |
| 4035799 | 5/1992 | Germany . |

OTHER PUBLICATIONS

Dimitri A. Parthenopoulos and Peter M. Rentzepis, "Three–dimensional Optical Storage Memory", Science, vol. 245 (Aug. 25, 1989), pp. 843–845.

(List continued on next page.)

*Primary Examiner*—Constantine Hannaher
*Assistant Examiner*—Andrew Israel
*Attorney, Agent, or Firm*—Jones, Tullar & Cooper

[57] ABSTRACT

A laser scanning microscope produces molecular excitation in a target material by simultaneous absorption of three or more photons to thereby provide intrinsic three-dimensional resolution. Fluorophores having single photon absorption in the short (ultraviolet or visible) wavelength range are excited by a beam of strongly focused subpicosecond pulses of laser light of relatively long (red or infrared) wavelength range. The fluorophores absorb at about one third, one fourth or an even smaller fraction of the laser wavelength to produce fluorescent images of living cells and other microscopic objects. The fluorescent emission from the fluorophores increases cubicly, quarticly or even higher power law with the excitation intensity so that by focusing the laser light, fluorescence as well as photobleaching are confined to the vicinity of the focal plane. Scanning of the laser beam by a laser scanning microscope allows construction of images by collecting multi-photon excited fluorescence from each point in the scanned object while still satisfying the requirement for very high excitation intensity obtained by focusing the laser beam and by pulse time compressing the beam. The focused pulses also provide three-dimensional spatially resolved photochemistry which is particularly useful in photolytic release of caged effector molecules, marking a recording medium or in laser ablation or microsurgery. This invention refers explicitly to extensions of two-photon excitation where more than two photons are absorbed per excitation in this nonlinear microscopy.

11 Claims, 3 Drawing Sheets

U.S. PATENT DOCUMENTS

| | | |
|---|---|---|
| 4,877,965 | 10/1989 | Dandliker et al. . |
| 4,887,721 | 12/1989 | Martin et al. . |
| 5,022,757 | 6/1991 | Modell . |
| 5,034,613 | 7/1991 | Denk et al. . |
| 5,196,709 | 3/1993 | Berndt et al. . |
| 5,239,178 | 8/1993 | Derndinger et al. . |
| 5,272,089 | 12/1993 | Vo-Dinh . |
| 5,289,407 | 2/1994 | Strickler et al. . |
| 5,376,246 | 12/1994 | Page . |
| 5,518,694 | 5/1996 | Bentsen . |
| 5,523,573 | 6/1996 | Hanninen et al. . |
| 5,777,732 | 7/1998 | Hanninen et al. . |

OTHER PUBLICATIONS

Hollas 1987, "Modern Spectroscopy", John Wiley & Sons 1987, pp. 308–309.

Sheppard & Kompfner 1978, "Resonant scanning optical microscope", Applied Optic Col. 17 (Sep. 15, 1978), pp. 2879–2882.

Antonov et al. 1982, "Multiple Photon Processes in Molecules Induced by picosencond UV Laser Pulses", in Picosecond Phenomena III—Proceedings of the Third International Conference on Picosecond Phenomena, Jun. 16–18, 1982, pp. 310–314.

Gannaway & Sheepard 1978, "Second–harmonic imaging in the scanning optical microscope", Optical and Quantum Electronics vol. 10 (1978), pp. 435–439.

Wilson & Sheppard 1979, "Imaging and super–resolution in the harmonic microscope" Optica Acta, vol. 26 (1979), pp. 761–770.

Demptroder 1981, "Laser Spectroscopy", Springer–Verlag 1981, pp. 422–441 and 672–675.

Janis A. Valdmanis and R. L. Fork, "Design Considerations for a Photon Second Pulse Laser . . . ", IEEE Journal of Quantum Electronics, vol. QE 22, No. 1, Jan. 1986, pp. 112–118.

C.V. Shank "Generation of Ultrashort Optical Pulses", Topics in Applied Physics, vol. 60, Jan. 1988, pp. 5–31(particularly p. 15).

C.J.R. Sheppard: "Scanning optical microscope", Electronics and Power, pp. 166–172, Feb. 1980. Reprinted in SPIE Milestone Series, vol. MS 131, pp. 113–119, as enclosed.

Patrick P. Galmettes and Michael W. Berns: "Laser–induced multiphoton processes in living cells", Proc. Natl. Acad. Sci. USA, vol. 80, pp. 7197–7199, Dec. 1983, Biophysics.

He, et al., "Three–Photon–Absorption–Induced Fluorescence and Optical Limiting Effects in an Organic Compound," Optics Letters, vol. 20 (No. 14), p. 1524–26, (Jul. 15, 1995).

Davey, et al., "Three Photon Induced Fluorescence from a Conjugated Organic Polymer for Infrared Frequency Upconversion," Applied Physics Letters, vol. 67 (No. 7), p. 884–885, (Aug. 14, 1995).

Pantell, et al., "Theoretical and Experimental Values for Two–, Three–, and Four–Photon Absorptions," The Journal of Chemical Physics, vol. 46 (No. 9), p. 3507–3511, (May 1, 1966).

Wokosin, et al., "Multi–Photon Excitation Imaging with an All–Solid–State Laser," SPIE, vol. 2678, p. 38–49, (Jan. 31, 1996).

Ohsawa et al., "On the Possibility of Gas Temperature Measurement Using Two Photon Excitation," Proceedings of the 8th IMEKO Congress of the International Measurement Confederation, p. 523–528, (May 21, 1979).

Fritzler et al., "A Spectrometer for Semiautomatic Two Photon Fluorescence Spectroscopy," Journal of Physics E: Scientific Instruments, vol. 8 (No. 6), p. 530–532, (Jun. 30, 1975).

Slomba et al., "A Laser Flying Spot Scanner for Use in Automated Fluorescence Antibody Instrumentation," Journal of the Association for the Advancement of Medical Instrumentation, vol. 6 (No. 3), p. 230–234, (May 30, 1972).

Parthenopoulos et al., "Three Dimensional Optical Storage Memory," Science, p. 843–845, (Aug. 25, 1989).

Wilson et al., "Theory and Practice of Scanning Optical Microscope," Academic Press (London), p. 8–9, (Nov. 30, 1984).

Seveus et al., "Time Resolved Fluorescence Imaging of Europium Chelate Label in Immunothistochemistry and In Situ Hybridization," Cytometry 13: 1329–38, (Nov. 30, 1992).

Peticolas et al., "Double Photon Excitation in Organic Crystals," Physical Review Letters, vol. 10 (No. 2), p. 43–45, (Jan. 15, 1963).

Hanninen et al., "Two Photon Excitation in Time–Resolved Fluorescence Microscopy," SPIE, p. 66–71, (Feb. 7, 1994).

MULTI-PHOTON LASER MICROSCOPY

The present application claims the benefit under 35 U.S.C. 119 (e) of U.S. Provisional Application No. 60/003,957, filed Sep. 19, 1995.

BACKGROUND OF THE INVENTION

The present invention relates to a laser microscopy technique which produces molecular excitation in a target material by simultaneous absorption of three or more photons. The invention is an improvement over the two-photon laser microscopy technique disclosed in U.S. Pat. No. 5,034,613 to Denk et al. (hereinafter, the '613 patent), and this patent is hereby incorporated by reference.

The '613 patent discloses a laser scanning microscope which produces molecular excitation in a target material by simultaneous absorption of two photons to provide intrinsic three-dimensional resolution. Fluorophores having single photon absorption in the short (ultraviolet or visible) wavelength range are excited by a stream of strongly focused subpicosecond pulses of laser light of relatively long (red or infrared) wavelength range. The fluorophores absorb at about one half the laser wavelength to produce fluorescent images of living cells and other microscopic objects. The fluorescent emission from the fluorophores increases quadratically with the excitation intensity so that by focusing the laser light, fluorescence and photobleaching are confined to the vicinity of the focal plane. This feature provides depth of field resolution comparable to that produced by confocal laser scanning microscopes, and in addition reduces photobleaching. Scanning of the laser beam, by a laser scanning microscope, allows construction of images by collecting two-photon excited fluorescence from each point in the scanned object while still satisfying the requirement for very high excitation intensity obtained by focusing the laser beam and by pulse time compressing the beam. The focused pulses also provide three-dimensional spatially resolved photochemistry which is particularly useful in photolytic release of caged effector molecules.

A drawback to the two-photon laser microscopy technique disclosed in the '613 patent is that its applications are limited by the available laser technology. In particular, the two-photon technique requires use of a laser at specific wavelengths, depending upon the application, so that the sum of energy levels of the two photons provides the specific energy level needed to generate the desired fluorescent emission. Unfortunately, some laser microscopy applications would require use of a laser having a wavelength which is not technologically feasible at the present time. For example, excitation of chromophores that have very short wavelength absorption, such as amino acids and nucleic acids, would require a laser having a 540 nm wavelength using the two-photon technique, and such a laser does not exist at the present time.

SUMMARY OF INVENTION

The present invention provides a solution to the aforementioned problem through the application of three or more photon excitation to laser scanning fluorescence microscopy and to spatially resolved photo-chemical processing, such as caged reagent activation for micropharmacology and polymer cross linking for 3-d optical information storage.

Because three-photon induced fluorescence obeys a cubic dependence on excitation intensity and four photon excitation obeys a quartic dependence, both provide intrinsic three-dimensional resolution in laser scanning microscopy. Although such 3-d resolution has already been achieved by the nonlinear microscopy technique based on two-photon excitation disclosed in the '613 patent, three-photon excitation provides a unique opportunity to excite molecules normally excitable in the UV range (230–350 nm) with near IR light (700–1100 nm). Interesting biomolecules, such as the amino-acids tryptophan and tyrosine, the neurotransmitter serotonin and nucleic acids, have one-photon absorption peaks at approximately 260–280 nm, and fluorescence can be excited in these biomolecules by three and four photon excitation. The advantages of using long wavelength, near IR light are possibly less photodamage to living cells and conveniently available solid state femtosecond laser sources for deep UV absorbers. In practice, the configuration of three-photon laser scanning microscopy can be identical to the existing two-photon systems. However, because three-photon and two-photon absorption spectra are in general quite different, the combination of two- and three-photon excited fluorescence microscopy extends the useful range of the laser systems currently employed in two-photon microscopy.

A particularly advantageous application of three or more photon excitation is the replacement of excimer lasers for certain applications which require absorption of wavelengths around 200 nm. Three and four photon excitation by lasers generating much longer wavelengths (say 550–900 nm) should provide similar energy absorption and provide 3-d spatial resolution as well. Because excimer lasers are extremely expensive and user unfriendly, several photon excitation could be highly desirable.

The practicality of the proposed three-photon microscopy depends crucially on the three-photon fluorescence excitation cross-sections of various fluorophores and biomolecules. However, very few three-photon absorption cross-sections have been reported. A simple calculation based on perturbation theory shows that three-photon excitation would typically need <10 times the peak intensity currently used with two-photon excitation technique to achieve a comparable level of excitation. This required intensity level can be easily accessed by femtosecond laser sources, such as the modelocked Ti:sapphire laser. Three-photon induced fluorescence of tryptophan and serotonin has been observed at excitation wavelengths between approximately 800 and 900 nm using a modelocked Ti:sapphire laser. The measured fluorescence obeys an expected cubic law dependence on excitation intensity. Measurements of fluorescence power of the calcium indicator dye Fura II at an excitation wavelength (approximately 911 nm) well below the expected three-photon excitation optimum, showed that satisfactory fluorescence images should be obtainable at only ~5 times the laser power required for two photon excitation of Fura II at its optimum excitation wavelength (approximately 730 nm). The estimated three-photon fluorescence excitation cross-section from these preliminary results shows that three-photon laser scanning microscopy can be done with a reasonable level of excitation power. How widely applicable this approach will be remains to be determined. Four-photon excitation may be limited by the onset of strong one-photon absorption by water above about 1000 nm.

Studies of molecular excitation of fluorescence by three or more photon processes are rare because the excitation cross sections have been expected to be quite small. Thus, useful rates of excitation usually require very high instantaneous illumination intensities. A simple extrapolation of multiphoton cross sections is suggested by the pattern of matrix elements products in the perturbation theory solutions of the quantum mechanics of the dipole transition probability for molecular excitation by a radiation field. Basically, the multiphoton processes require three or more photons to interact with the molecule (within the cross sectional area of a molecule, $A \sim 10^{-16}$ cm$^2$) and simultaneously (within a time interval determined by the life times of intermediate states, $\delta\tau \sim 10^{-16}$s). This short coincidence time is limited by the large energy uncertainties introduced by the perturbation theory energy denominators.

Fluorescence excitation by several photons does not significantly increase laser microscopy resolution because the longer excitation wavelength (for a given fluorophore) decreases resolution by about as much as it is increased by raising the one-photon point spread function to the power n for several-photon processes. Were it not for the wavelength factors, the increase in resolution of three photon excitation would be essentially the same as that incurred by adding an ideal confocal spatial filter to two photon microscopy.

Recent reports of unexpectedly large three-photon cross sections have been found in the course of research directed toward enhancing optical limiting absorption (which is intended to provide variable shades for protection of human vision from excessively brilliant light flashes). Recently, a three photon absorption cross section of about $10^{-75}$ cm$^6$s$^2$ has been reported for absorption and fluorescence of 2,5-benzothiazo 3,4-didecyloxy thiophene in tetrahydrofuran. Another recent experiment shows three photon excitation of fluorescence from a conjugated organic polymer. This process, however, appears to involve two excitation states unlike most fluorescence excitation. Although the conditions of these experiments are hardly suitable for laser scanning fluorescence microscopy or for most microphotochemistry, the large cross sections are promising. Note, however, that such large cross-sections are not essential for three or more photon microscopy.

The excitation wavelength dependence of the rate of photodamage to living cells during fluorescence microscopy and photo-micropharmacology is largely unknown and may vary greatly for different applications. Empirical studies have shown that two-photon excitation elicits far less damage than one-photon excitation for comparable fluorescence image-acquisition. It is not clear whether further improvement can be made by stepping up to three- or four-photons for excitation. With the aid of such knowledge and the knowledge of the nonlinear absorption spectra, it is conceivable that the optimum excitation mode can be determined and utilized for each individual system in the future. A particularly appealing possibility is the use of one laser wavelength to induce photochemistry by three photon excitation and concurrently two-photon excitation of an accompanying fluorescence signal. Three-photon excitation seems quite likely to become a useful enhancement of the existing two-photon excitation technique but seems unlikely to replace it.

Alternatively, for microscopic photochemical activation, photoablation and optical surgery, the photo excitation can be advantageously accomplished by multi-photon excitation of intrinsic chromophores or even added chromophores that have very short wavelength absorption such as amino acids and nucleic acids. Multi-photon excitation allows the selection of more available lasers providing subpicosecond pulses at long wavelengths and long wavelength light transmission to the microscopic focal volume where photo excitation is desired.

BRIEF DESCRIPTION OF THE DRAWINGS

The foregoing and additional features and advantages of the present invention will become apparent from the following detailed description of a preferred embodiment thereof, taken in conjunction with the accompanying drawings, in which.

BEST MODE FOR CARRYING OUT THE INVENTION

Figure 1:
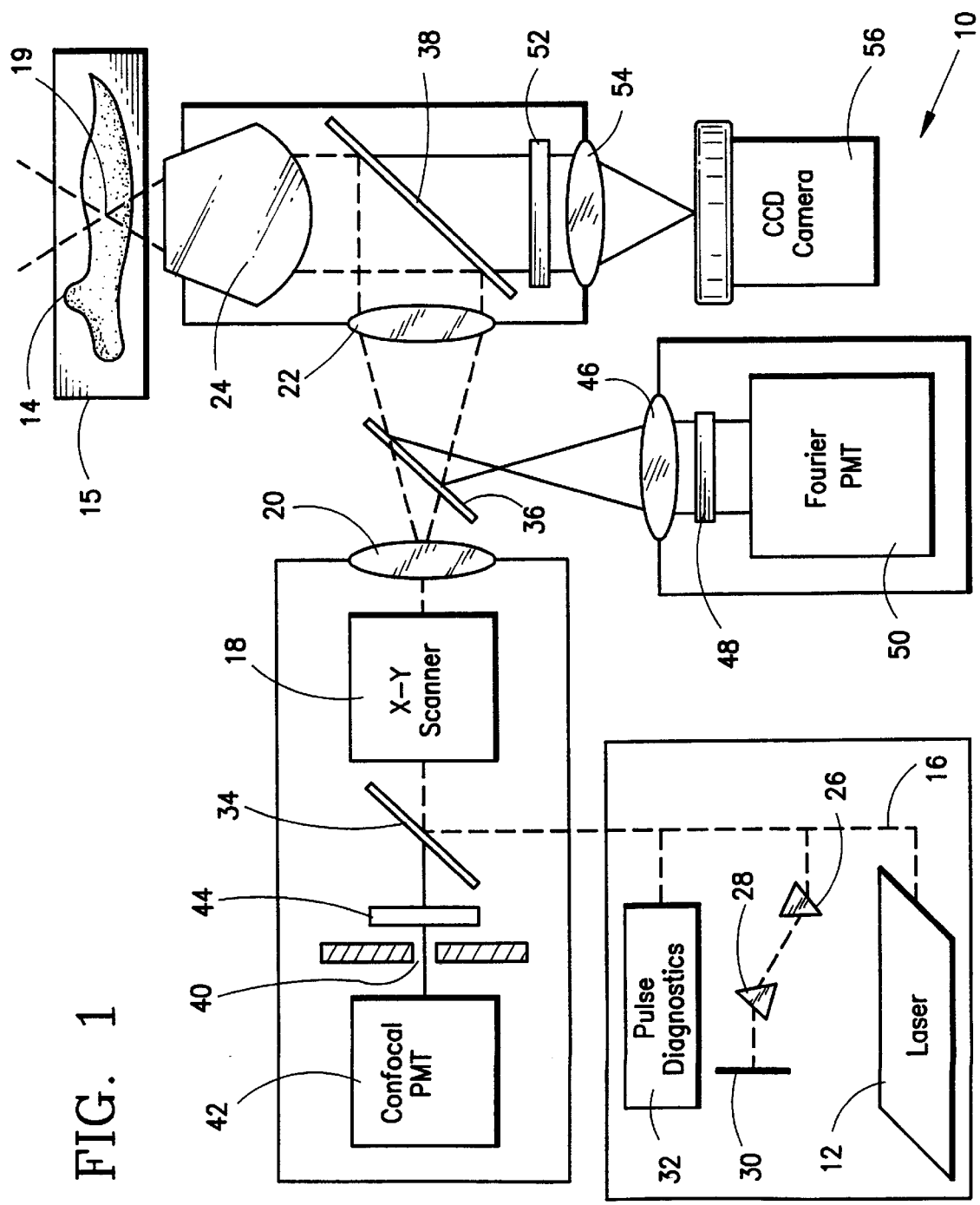
FIG. 1 is a diagrammatic illustration of a laser scanning microscope utilized in accordance with a preferred embodiment of the present invention.

Turning now to a detailed description of a preferred embodiment of the present invention, FIG. 1 illustrates in diagrammatic form a conventional laser scanning microscope 10 which includes three detection alternatives. A subpicosecond pulsed laser source 12 provides the necessary excitation of a specimen or target material 14 which is positioned on a movable stage or other suitable support 15. The laser 12 may be, for example, a colliding pulse, mode-locked dye laser or a solid state laser which can generate pulses of light having a wavelength in the red region of the spectrum, for example about 630 nm, with the pulses having less than 100 fsec duration at about 80 MHz repetition rate. Other bright pulsed lasers may also be used to produce light at different relatively long wavelengths in the infrared or visible red region of the spectrum, for example, to generate the necessary excitation photon energies whose sum will equal the appropriate absorption energy band required by the fluorophores in the specimen. In a single photon excitation technique, these would be excited by absorption of a single photon in the spectral region having wavelengths approximately one third or one fourth the wavelength of the incident light, for three and four photon excitation, respectively. Thus, for example, three photons in the visible red region at 945 nm would combine to excite a fluorophore which normally absorbs light in the ultraviolet region at 315 nm, while three photons at 1070 nm would excite a molecule which absorbs at 357 nm in the visible light region.

In a modified form of the invention, the single wavelength laser 12 can be replaced by two or more different long wavelength laser sources so that the incident light beam consists of two or more superimposed pulsed light beams of high instantaneous power and of different wavelengths. The wavelengths of the incident beam are selected to excite a fluorophore which is absorbent at a short wavelength which may be described as:

$$1/\lambda_{abs} = 1/\lambda_1 + 1/\lambda_2 + 1/\lambda_3$$

where $\lambda_{abs}$ is the short wavelength of the absorber, and $\lambda_1$, $\lambda_2$ and $\lambda_3$ are the laser incident beam wavelengths for the three wavelength case.

The laser 12 generates a pulsed output beam 16 which is scanned by an X–Y scanner 18 comprising a set of oscillating mirrors, and is then focused onto the specimen 14 at a focal point or volume 19 therein by a pair of eyepiece lenses 20 and 22, and an objective lens 24. The objective lens' back aperture is a pivot point for the scanned beam so, neglecting aberrations, all points in the raster pattern experience equivalent imaging conditions. The scanner 18 causes scanning of the focal point or volume 19 through the material 14, thereby causing fluorescence excitation of the material 14 at or near the focal point or volume 19.

Before the output beam 16 is directed into the X–Y scanner 18, it undergoes both dispersion compensation and pulse diagnostics. One complication of femtosecond pulsed illumination is dispersion. Short pulses tend to be broadened when passing through optical materials because differing frequency components of the pulse band width travel at different speeds within the materials. Dispersion compensation for optical materials is not essential for pulses greater than about 120 fsec, as these pulses have a small frequency band width (about 4 nm) and thus experience little spreading. However, a 700 nm, 70 fsec pulse is found to be spread about 1.5 times by a good objective lens, and substantially more by standard acousto-optical modulators that may be used for beam modulation and shutters. Pulse broadening reduces the observed fluorescence proportionality. In the microscope 10, dispersion compensation for optical materials is effected by a double pass through a pair of glass prisms 26 and 28 that direct the light so that the higher (in general slower) frequencies travel through less glass and are thus restored to the appropriate phase lag. A totally reflecting mirror 30 is employed to provide the return pass through the prisms 26 and 28.

For quantitative measurements, it is necessary to know the wavelength and pulse duration of the excitation beam, and thus various forms of pulse diagnostics 32 are provided to analyze the pulsed output beam 16. For a rough monitor of both wavelength and duration, a simple monochromator which, in its standard configuration, provides wavelength measurement, is sufficient. If the output slit is removed and the resulting spectrum is sent to a screen or a one dimensional detector, the pulse wavelength band can be monitored. For a more precise pulse analysis, the pulse diagnostics 32 can comprise an autocorrelator which enables a direct, detailed measure of the pulse width and an indication of its phase coherence profile.

The laser microscope 10 also includes first, second and third dichroic mirrors 34, 36 and 38 which are employed to split off the fluorescence pathway for each of the three detector alternatives. The first of these alternatives is known as descanned confocal detection. In confocal detection, the fluorescence beam is descanned to form a stationary image plane at a pinhole aperture 40 placed before a confocal photomultiplier tube (PMT) 42. At every position in the scan, the point being illuminated in the sample focuses to, or is confocal to, the aperture in the detector plane. A band pass emission filter 44 is positioned between the pinhole aperture 40 and the first dichroic mirror 34 to eliminate undesired frequencies from the detected signals.

The second detection technique is known as Fourier plane detection in which the objective back aperture is focused through a lens 46 and a band pass emission filter 48 onto a Fourier PMT 50 without descanning. Because the back aperture is a pivot point in the scan, the fluorescence pattern is stationary at the photocathode.

Finally, the third detection technique is known as scanned imaging detection in which the entire focal plane in the specimen 14 is focused through a band pass emission filter 52 and a focusing lens 54 onto an imaging detector 56, such as a CCD camera, whose acquisition speed is synchronized to the frame scan time.

The initial choice of detection method may be dictated by an existing microscope setup or by the microscopy method necessary for the specific experiments planned. Each detection scenario offers its own particular advantages and disadvantages. In all of these detection scenarios, the collected fluorescence is extracted by an appropriately coated dichroic mirror. Because the difference between excitation and emission wavelengths is typically much greater than the Stokes shift, the dichroic coating need not have the usual sharp cut-on between the reflection transmission bands. The emission filters 44, 48 and 52 are usually standard, although they need to be checked for proper rejection at the multi-photon excitation wavelengths. Because the ratio of the average excitation power to the fluorescence power is higher in multi-photon laser microscopy than in linear microscopies, a higher rejection ratio is required. Photomultiplier selection for a red-insensitive photoelectron emitter is therefore beneficial.

For multi-photon excitation with more than two photons, say with N photons, the number of photons absorbed per pulse per fluorophore can be written generally as:

$$^N n_a \approx \left[ \frac{P_O^N \, ^N\delta}{(\tau f)^{N-1} f} \left( \frac{A^2}{2hc\lambda} \right)^N \right]$$

where the pre-superscript N designates the number of photons simultaneously absorbed in analogy in the two photon excitation case where N=2 described above. The ratio $^N n_a / ^{(N-1)} n_a$ of successive rates for the multi-photon absorption process provides a useful comparison parameter of the form $$\frac{^N n_a}{^{(N-1)} n_a} = \frac{P_O}{(hc/\lambda)} \cdot \frac{1}{\tau f} \cdot \frac{^N \delta}{^{(N-1)} \delta} \cdot \frac{A^2}{2} \cdot \frac{1}{\lambda^2}$$

Favorable values of the expected absorption cross sections are tabulated below.

| Number of Photons n | (Area)$^n$ A$^n$ (cm$^{2n}$) | (coincidence time)$^{n-1}$ ($\delta\tau$)$^{n-1}$ | Excitation Cross Section | Units |
| --- | --- | --- | --- | --- |
| 1 | $10^{-16}$ cm$^2$ | 1 | $\sigma = 10^{-16}$ | cm$^2$ |
| 2 | $10^{-32}$ cm$^4$ | $10^{-17}$ s | $\delta = 10^{-49}$ | cm$^4$ (s/photon) |
| 3 | $10^{-48}$ cm$^6$ | $10^{-34}$ s$^2$ | $\gamma = 10^{-82}$ | cm$^6$ (s/photon)$^2$ |
| 4 | $10^{-64}$ cm$^8$ | $10^{-51}$ s$^3$ | $\epsilon = 10^{-115}$ | cm$^8$ (s/photon)$^3$ |

With these typical values of the multi-photon cross sections and the instrument parameters described for two-photon excitation above, the absorption ratio is unity at about 3 W laser power. However, this equal emission power depends specifically on the wavelength dependent cross sections. Higher ratios $N\delta/^{N-1}\delta$ exist for known favorable fluorophores and more may be found in research motivated by this invention and by other applications of multi-photon absorption. In applications to biological cells and tissues, the selection of higher order multi-photon excitation process and optimization of excitation wavelength provides a means to select conditions suitable to minimize biological photodamage during fluorescence microscopy and microscopic activation of caged compounds. For multi-photon laser microscopy or photochemistry the selection of higher order multiphoton processes accommodates selection of available laser wavelengths.

With multi-photon excitation with N>2 the imaging resolution is improved relative to two-photon excitation since the microscope point spread function, which defines resolution, is multiplied by itself to the power N. Thus for three-photon excitation the resolution is further improved by nearly the same factor as insertion of an infinitesimal confocal aperture, neglecting wavelength factors which do reduce resolution as wavelengths increase.

Figure 2:
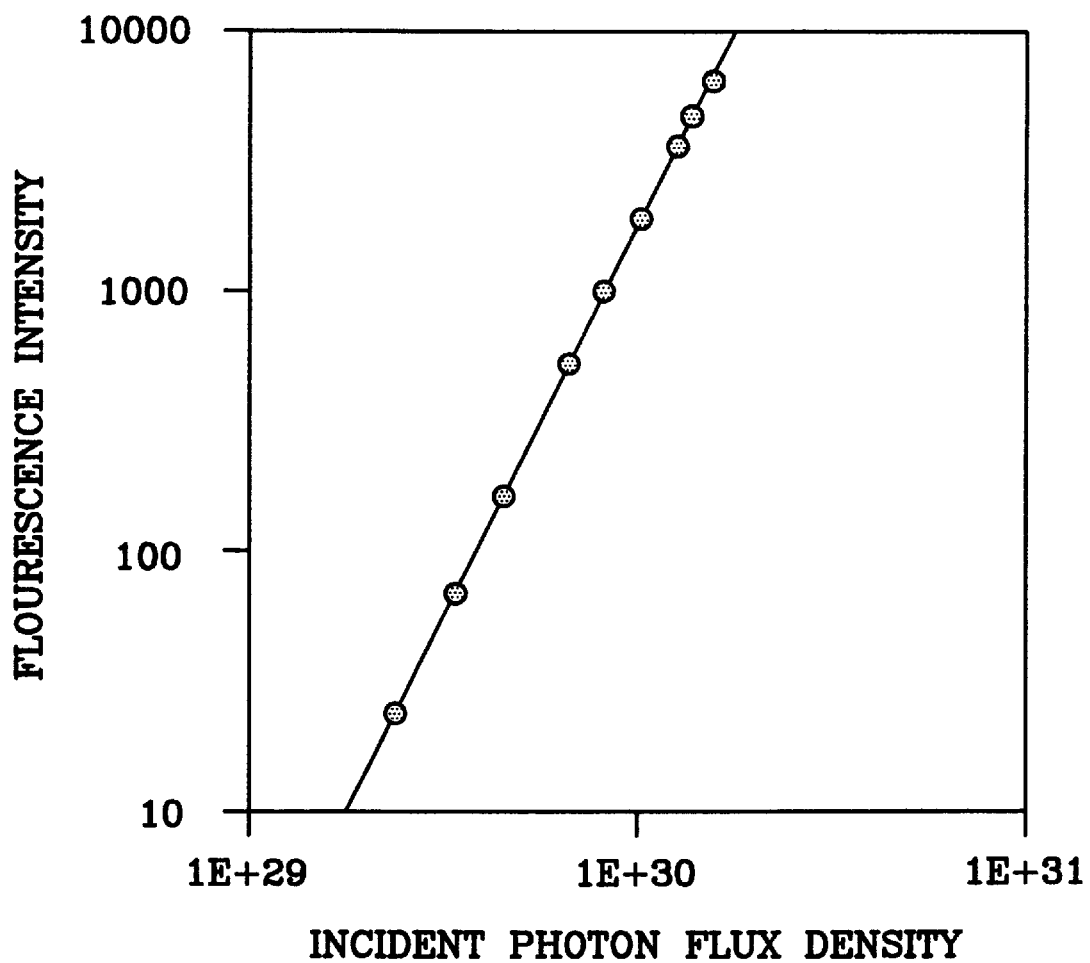
FIGS. 2 and 3 are graphs of the average fluorescence intensity versus the applied peak laser flux density obtained utilizing three-photon excitation of Fura-2 and Indo-1, respectively.
Figure 3:
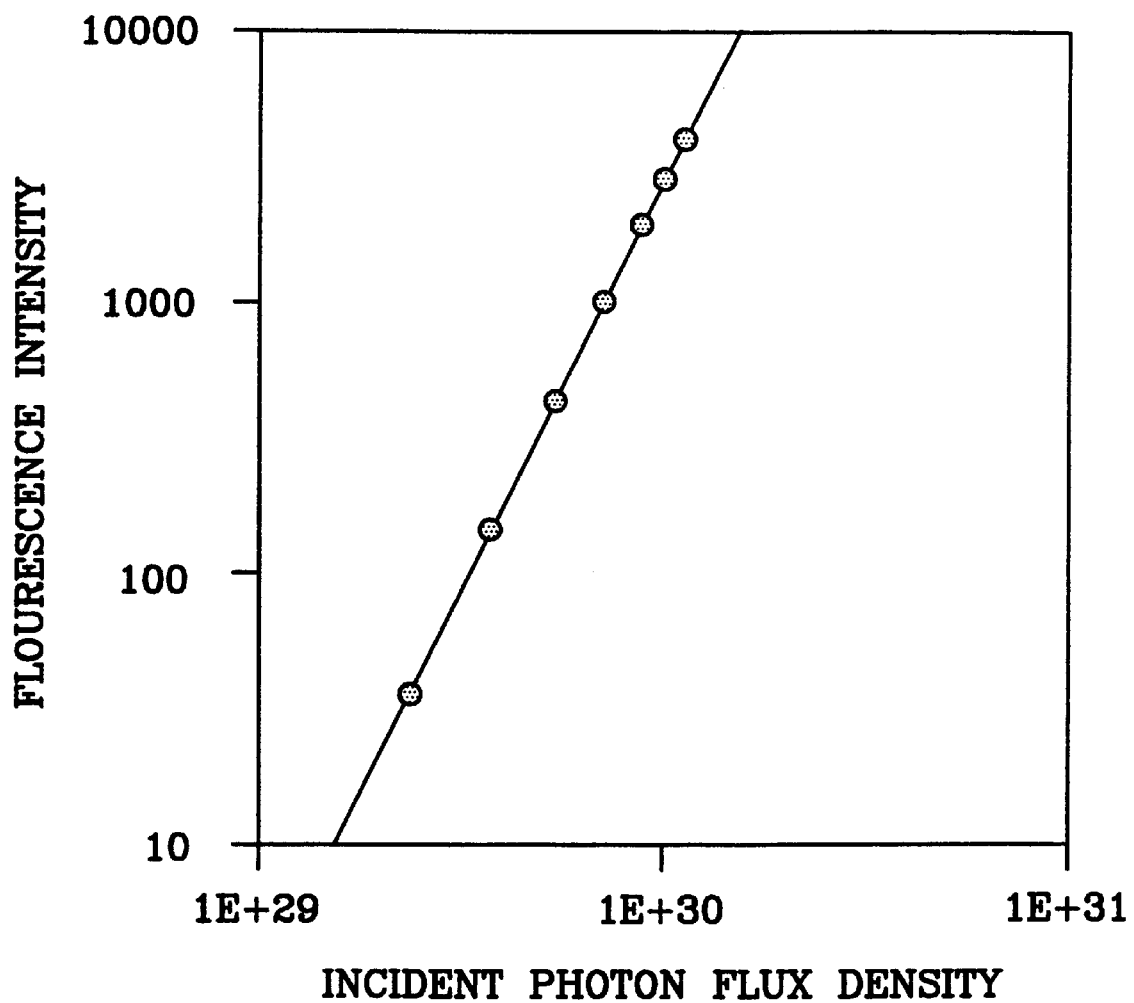

FIGS. 2 and 3 illustrate the fluorescence intensity as a function of the incident photon flux density for three-photon excitation of Fura-2 at 1.0 μm, and Indo-1 with Ca at 1.0 μm, respectively. In both cases, the fluorescence intensity increases in proportion to the cube of the incident photon flux density, clearly indicating three-photon excitation in the test materials.

Another advantage of multi-photon excitation by three or more photons, is that the favorable properties of two photon excitation are further enhanced in higher order processes because dependence of out of focus excitation falls off as successively higher powers N of the intensity with increasing values of photon order N.

Since three or more photon excitation in accordance with the present invention provides access by visible or infrared light to excitation energies corresponding to single-ultraviolet-photon excitation, a whole new class of fluorophores and fluorescent indicators becomes accessible to three-dimensionally resolved laser scanning microscopy. Although three or more photon cross sections are not yet known for many compounds, and different selection rules apply to three or more photon absorption, molecular asymmetry often allows both odd and even photon transitions into the same excited state. It has been found that effects of excited state symmetry do appear to shift the relative values of odd photon and even photon absorption cross section peaks. Thus, an absorption peak for two-photon absorption sometimes appears at a significantly shorter wavelength than twice the dominant absorption peak for the one-photon process, and the wavelength dependence of three-photon absorption can resort to a wavelength dependence like thrice the one-photon case. Multi-photon excitation may be particularly strong in the case of incoherent multi-step excitation where absorption of one energy (say by absorption of two-photons) reaches an intermediate state from which a subsequent additional photon provides the energy to reach a state from which fluorescence or photochemical activation can occur.

Now all of the above fluorophores are routinely used for imaging fluorescent label distributions in living cells with two-photon excitation. Three-photon excitation of comparable fluorescence intensities have been obtained with Indo-1, FURA-2, DAPI and darnyl. The three-photon absorption cross sections are approximately $^3\delta \sim 2 \times 10^{-82} cm^6$ (S/photon)$^2$. Three- and four-photon excitation of fluorescent amino acids in serotonin, norepinepherine and tryptophan have been measured with red light excitation with one-photon absorption occurring below 300 nm. The use of three- and four-photon excitation by available lasers provides an advantage in microscale detecting and imaging of scarce neurotransmitters and hormones.

Another application of the present invention is as a method for producing microscopically localized ablation of tissue or tissue organelles for their destruction or surgical removal. This is accomplished through use of the three or more photon absorption either by intrinsic chromophores, or by extrinsically provided chromophores that label the tissue and provide first characteristic energies for absorption of subpicosecond pulses of laser light providing the second characteristic energy which is about an integer fraction, i.e., one third, one fourth, etc., or less of the first characteristic energy. Alternatively, the molecules providing the necessary fluorescence can be intrinsic tissue fluorophores.

Although the present invention has been disclosed in terms of a preferred embodiment, it would be understood that numerous modifications and variations could be made thereto, without departing from the scope of the invention as defined in the following claims.

What is claimed is:

1. A method of microscopy by a three or more photon excitation technique of a target material containing molecules which are excitable by photons of a characteristic energy comprising the steps of:
   illuminating said material with a beam of intense, subpicosecond pulses of laser light comprising photons of an energy approximately 1/n of said characteristic energy, where n equals a number of photons to be absorbed by said material and is greater than or equal to three; and
   focusing said illumination within said material to produce an illumination intensity sufficiently high to produce molecular excitation by simultaneous absorption of at least three of said incident illuminating photons.

2. The method of claim 1, wherein said material includes caged biologically active molecules, said illumination intensity being sufficient to release caged biologically active compounds by simultaneous absorption of n incident photons, each of energy equal to approximately 1/n of said characteristic energy.

3. The method of claim 1, wherein said material includes fluorescent molecules, said illumination intensity being sufficient to produce fluorescence of said material by simultaneous absorption of n incident photons, each of energy equal to approximately 1/n of said characteristic energy.

4. The method of claim 3, wherein said step of focusing said illumination further comprises focusing said illumination to a small focal volume within said material to produce illumination intensity sufficiently high only at said focal volume to produce molecular excitation by simultaneous absorption of said n of said incident illuminating photons.

5. The method of claim 4, further including the steps of:
   scanning said beam to scan said focal volume through said material; and
   detecting the fluorescence produced by said material.

6. The method of claim 1, wherein said material is a tissue, and said molecular excitation occurs by simultaneous absorption of at least three of said incident illuminating photons by intrinsic chromophores, extrinsically provided chromophores or intrinsic fluorophores within said tissue.

7. An apparatus for laser scanning fluorescence microscopy of a target material including a fluorescent component responsive to excitation by photons of a characteristic energy to produce fluorescence photons, said apparatus comprising:
   stage means for receiving said target material;
   at least one source of subpicosecond coherent light pulses comprised of energy 1/n of said characteristic energy, where n is greater than or equal to three;
   means for focusing said coherent light pulses on said target material, thereby causing said target material to absorb at least three photons and produce said fluorescence photons;
   detector means for detecting said fluorescence photon; and
   means for directing said fluorescence photons to said detector means.

8. The apparatus of claim 7, further including scanning means for scanning said light pulses through said material.

9. The apparatus of claim 7, wherein said detector means comprises a confocal photomultiplier tube.

10. The apparatus of claim 7, wherein said detector means comprises a Fourier plane detector.

11. The apparatus of claim 7, wherein said detector means comprises an imaging detector.

* * * * *